US009863859B2

(12) United States Patent
Whittington et al.

(10) Patent No.: US 9,863,859 B2
(45) Date of Patent: Jan. 9, 2018

(54) SERPENTINE LOAD MONITORING APPARATUS

(71) Applicant: Mississippi State University Research and Technology Corporation, Starkville, MS (US)

(72) Inventors: Wilburn Ray Whittington, Starkville, MS (US); Andrew Lars Oppedal, Starkville, MS (US)

(73) Assignee: Mississippi State University Research and Technology Corporation, Mississippi State, MI (US)

(*) Notice: Subject to any disclaimer, the term of this patent is extended or adjusted under 35 U.S.C. 154(b) by 34 days.

(21) Appl. No.: 14/694,463

(22) Filed: Apr. 23, 2015

(65) Prior Publication Data
US 2015/0308932 A1 Oct. 29, 2015

Related U.S. Application Data

(60) Provisional application No. 61/983,120, filed on Apr. 23, 2014.

(51) Int. Cl.
*G01N 3/02* (2006.01)
*G01N 3/08* (2006.01)
*G01N 3/06* (2006.01)
*G01L 1/22* (2006.01)
*G01L 5/00* (2006.01)

(52) U.S. Cl.
CPC ............. *G01N 3/08* (2013.01); *G01L 1/2218* (2013.01); *G01L 5/0038* (2013.01); *G01N 3/062* (2013.01)

(58) Field of Classification Search
CPC ..... G01L 1/2218; G01L 5/0038; G01N 3/062; G01N 3/08
See application file for complete search history.

(56) References Cited

U.S. PATENT DOCUMENTS

| | | | | | |
|---|---|---|---|---|---|
| 2,900,818 | A | * | 8/1959 | Starr | G01N 3/08 73/779 |
| 5,332,072 | A | * | 7/1994 | Crannage | B64C 27/001 188/372 |
| 6,009,670 | A | * | 1/2000 | Howard | E01F 13/06 49/226 |
| 6,116,077 | A | * | 9/2000 | Albertini | G01N 3/30 73/12.05 |
| 6,343,502 | B1 | * | 2/2002 | Subhash | G01N 3/58 73/81 |

(Continued)

OTHER PUBLICATIONS

Gilat, A., et al., "A New Compression Intermediate Strain Rate Testing Apparatus,", 14th International Conference on Experimental Mechanics, EDP Sciences, 2010, pp. 1-6.

Primary Examiner — David Bolduc
(74) Attorney, Agent, or Firm — Lawrence Arthur Schemmel

(57) ABSTRACT

Disclosed are various embodiments of systems and methods related to a load monitoring apparatus for testing of a material. The load monitoring apparatus may comprise a primary bar and one or more nested tubes substantially surrounding a portion of the primary bar. The one or more nested tubes are connected in series at alternate ends of the one or more nested tube. Further, the primary bar may comprise one or more sensors used to extract load sampling and monitor reflections of signals traversing the load monitoring apparatus.

20 Claims, 2 Drawing Sheets

(56) References Cited

U.S. PATENT DOCUMENTS

| | | | |
|---|---|---|---|
| 2003/0164022 A1* | 9/2003 | Vaidyanathan | G01N 3/307 73/12.01 |
| 2004/0129078 A1* | 7/2004 | Kicher | G01P 15/123 73/514.14 |
| 2009/0052066 A1* | 2/2009 | Kwan | G02B 7/005 359/823 |
| 2012/0306492 A1* | 12/2012 | Stautner | H01F 6/04 324/309 |

* cited by examiner

SERPENTINE LOAD MONITORING APPARATUS

CROSS REFERENCE TO RELATED APPLICATIONS

This application claims priority to copending U.S. Provisional Patent Application titled "SERPENTINE HOPKINSON TRANSMITTED BAR" filed on Apr. 23, 2014 and assigned application No. 61/983,120, which is incorporated by reference herein in its entirety.

BACKGROUND

The mechanical response of engineering materials depends on an applied strain rate. The stress-strain behavior of a material may be strongly strain rate dependent, such that calibrating and validating the constitutive model at the actual strain rate of interest are important if finite element analyses are used for components that experience these strain rates. Testing materials at a low-strain rate (i.e., below 5 $s^{-1}$) may be accomplished with conventional electromechanical or servo-hydraulic load frames. Testing materials at a high strain rate (i.e., above 500 $s^{-1}$) may be performed with the split Kolsky/Hopkinson pressure bar (SHPB) and/or other types of devices. However, testing materials within the intermediate strain rate regime requires the use of specially instrumented servo-hydraulic load frames or very long Hopkinson bars.

SUMMARY

Included are apparatuses for a load monitoring bar apparatus for use in dynamic testing of a material. One embodiment of an apparatus, among others, includes a load monitoring apparatus for use in dynamic testing of a material, the load monitoring apparatus comprising: a solid rod extending from a proximate end to a distal end; a first hollow rod substantially surrounding a portion of the solid rod, the first hollow rod being coupled to the distal end of the solid rod at a first connection point; and a second hollow rod substantially surrounding the first hollow rod, the second hollow rod being coupled to the first hollow rod at a second connection point, the second connection point being at an opposite end of the first hollow rod from the first connection point.

Another embodiment of an apparatus, among others, includes a load monitoring apparatus for testing of a material, the load monitoring apparatus comprising: a primary bar, a first sensor and a second sensor attached to the primary bar; and one or more nested tubes substantially surrounding a portion of the primary bar, the one or more nested tubes being connected in series at alternate ends of the one or more nested tubes.

Another embodiment of an apparatus, among others, includes a load monitoring apparatus for use in dynamic testing of a material, the load monitoring apparatus comprising a solid rod and a. plurality of nested tubes substantially surrounding a portion of the solid rod, the plurality of nested tubes being connected in series at alternate ends of the plurality of nested tubes, a first nested tube of the plurality of nested tubes being directly disposed around the portion of the solid rod and connected to the solid rod via a connection point at an end of the solid rod.

Other embodiments, systems, methods, features, and advantages of this disclosure will be or will become apparent to one with skill in the art upon examination of the following drawings and detailed description. It is intended that all such additional apparatuses, methods, features, and advantages be included within this description and be within the scope of the present disclosure.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
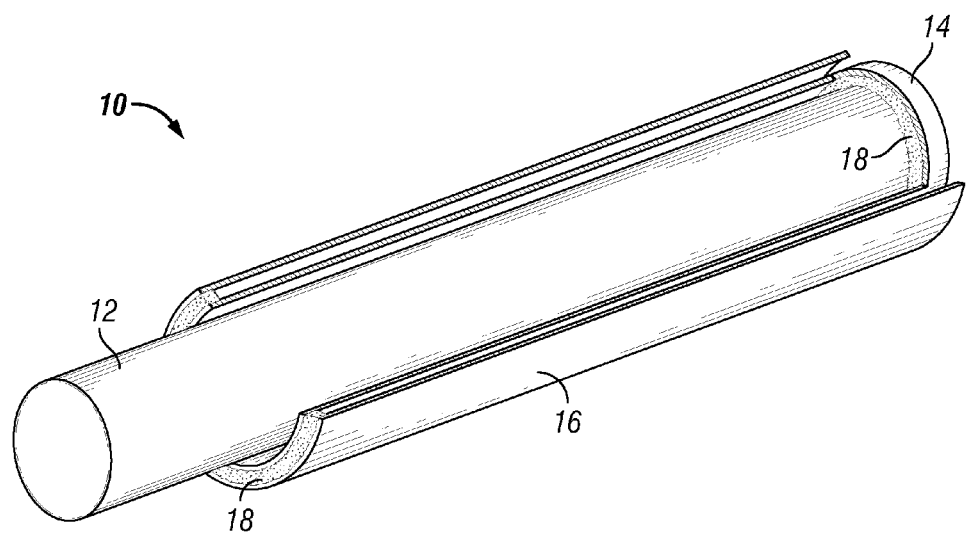
FIG. 1 is a drawing of an example of a load monitoring apparatus 10 illustrating a cross section of nested tubes surrounding a solid rod according to various embodiments of the present disclosure.

In the following discussion, a general description of apparatuses and methods according to various embodiments of the present disclosure is provided, followed by a discussion of the operation of the same. Embodiments of the present disclosure relate to a load acquisition bar apparatus used for obtaining strain-stress measurements. More specifically, disclosed herein are novel approaches to the implementation of a load monitoring apparatus used for measuring the dynamic force-motion, stress and strain relation, and energy of waves moving through solid objects.

By connecting alternate ends of a series of impedance matched tubes surrounding a solid rod, the load monitoring apparatus of the present disclosure is capable of producing useful stress-strain measurements in the intermediate strain rate regime while minimizing size constraints of known devices in conventional laboratories. The load monitoring apparatus may also produce repeatable stress-strain results while reducing stress oscillations typical of a specially instrumented servo-hydraulic load frame and produce data for a longer loading time than a conventional Kolsky/Hopkinson bar of the same effective length.

In the following disclosure, various embodiments are described. It is to be understood that those embodiments are example implementations of the disclosed invention and that alternative embodiments are possible. All such embodiments are intended to fall within the scope of this disclosure.

The mechanical response of engineering materials is widely known to depend on the applied strain rate. In high strain rate testing (500 $s^{-1}$ to 5000 $s^{-1}$), the split Hopkinson pressure bar (SHPB) may be used to gather the stress-strain behavior. In these tests, a specimen is placed between two bars, and a single shock wave is imparted to the specimen. Using sensors attached to the bars, stress strain relations may be extracted from monitoring of the bars.

One drawback of this type of testing is that the time duration of the test is limited to the length of the bars. The size constraints of the bar for testing at intermediate rates occurs because the stress wave propagates along the bar length, reflects off of the free end, and returns to the specimen. Once the stress wave reaches the specimen, the energy applied to the specimen changes and can subsequently change the applied strain rate, commonly known as a strain rate jump. Standard Hopkinson bar experiments are performed at such a high strain rate that the test is completed before the stress wave traverses the bar so as to eliminate this strain rate jump effect. Because of this size constraint, the standard Hopkinson bar has a lower strain rate limit for the bar setup. The minimum strain rate that can be achieved with a single continuous applied load in any bar system is described by the following:

$$\dot{\varepsilon}_{min} = \frac{\varepsilon_{max} C}{2L} \quad (1)$$

where L is the length of the transmitted bar, C is the longitudinal wave speed of the bar material, and $\varepsilon_{max}$ is the maximum strain incurred by the specimen. To reduce the minimum strain rate achievable in the test, the maximum strain may be reduced without changing the bar properties at all. However, reducing the maximum specimen strain preempts an experiment from achieving specimen failure. The longitudinal wave speed of the standard Hopkinson bar may be reduced by changing the bar material. However, materials with a significant reduction in wave speed, such as polymeric materials, also have a significant reduction in strength which cannot be used for testing metals that are stronger than the bars themselves. Bar length may also be adjusted. However, changing the bar length can be performed only to the extent that a laboratory can accommodate such a testing apparatus. To achieve strain rates in the intermediate strain rate regime (5 s$^{-1}$ to 500 s$^{-1}$), the testing apparatus would become too large to fit in conventional laboratories.

Known SHPBs have been modified to provide a long loading duration with hydraulic or other means with load acquisition using two or more strain gages on each bar to monitor the stress-strain relationship. In these systems, a multi-gage solution to the stress wave propagation allows stress-strain measurements to be captured after the stress wave has traversed the short transmitted bar multiple times. This method, however, presents a new problem as the strain rate jumps at every instance that the initial transmitted wave comes into contact with the specimen, and the reduced data may have many oscillations at intermediate strain rates.

Another known approach to testing materials in the intermediate strain rate regime is to modify existing low strain rate testing equipment. The desired loading rate of the specimen is realized by servo-hydraulics, while the sample grips and fixtures are modified to improve the load acquisition. A known modification of the fixtures is to design the load train with a high natural frequency such that the test frame reaches equilibrium along with the specimen. The load may be measured by a strain gage mounted on the fixture or grip section of the specimen or by using a small piezoelectric load washer. Although modified servo hydraulics may be rated for higher loading rates (10 ms$^{-1}$), at strain rates above 100 s$^{-1}$, these systems become unreasonably difficult to acquire load data.

Referring now to FIG. 1, shown is a drawing of an example of load monitoring apparatus 10, according to various embodiments of the present disclosure. The load monitoring apparatus 10 overcomes limitations of intermediate strain rate testing associated with conventional devices. Specifically, the load monitoring apparatus 10 comprises a series of concentric tubes substantially surrounding a solid rod to form a load acquisition bar that has the effective length of a conventional bar required for intermediate strain rate testing in a shorter actual length.

The load monitoring apparatus 10 of FIG. 1 comprises a solid rod 12, a first tube 14, and a second tube 16. The solid rod 12 may comprise steel, steel alloy, aluminum, aluminum alloy, titanium, titanium alloy and/or any other suitable material for the type of desired testing. The solid rod 12 extends from a proximate end to a distal end. During compression testing, a specimen 20 (FIG. 2) may be situated about the proximate end of the solid rod 12. Upon impact to the specimen 20 from another device, such as an incident bar of a conventional Hopkinson bar or other preferred device, waves generated by the impact may traverse through the serpentine bar starting at the proximate end of the solid rod 12 to the distal end of the second tube 16.

The first tube 14 substantially surrounds a portion of the solid rod 12. The distal end of the first tube 14 is connected to the distal end of the solid rod 12. The distal end of the solid rod 12 may be defined as the end of the bar opposite of the end of the solid rod 12 that is attached to the specimen 20 during testing. The second tube 16 substantially surrounds the first tube 14 such that the first tube 14 is nested within the second tube 16. The proximate end of the second tube 16 is connected to the proximate end of the first tube 14. Accordingly, the tubes are connected at alternating ends to create a folded, serpentine-like configuration such that the load monitoring apparatus 10 has the effective length of a conventional bar in an actual smaller length. The nested configuration allows the load monitoring apparatus 10 to behave as if it were a conventional Hopkinson bar having a longer actual length. Accordingly, upon impact to a specimen 20, waves being transmitted through the bar may traverse along the solid rod 12 and through each connected tube.

The distal end of the first tube 14 is connected to the distal end of the solid rod 12 and the proximate end of the first tube 14 is connected to the proximate end of the second tube 16 at respective connection joints 18. The alternating connecting joints 18 may be connected via welding with filler, welding without filler, glue, a screwed connection, a threaded connection, press fitting, forging, and/or any other appropriate type of connection that would generate accurate measurements. It should be noted that the connection joints 18 are preferred to be stiff and small to reduce the joint reflections.

The first tube 14 and the second tube 16 may each comprise a hollow tube-shaped member of steel, steel alloy, aluminum, aluminum alloy, titanium, titanium alloy and/or any other suitable material for the type of desired testing. The first tube 14 and the second tube 16 are impedance matched to the solid rod 12 to eliminate the reflection due to the added tubes. In addition, the first tube 14 and the second tube 16 are sized such to substantially match the cross-sectional area of the solid rod 12. The use of the first tube 14 and the second tube 16 multiplies the effective length of the load monitoring apparatus 10 by a factor of three. It should be noted that while the load monitoring apparatus 10 of FIG. 1 comprises two tubes 14, 16 substantially surrounding a portion of the solid rod 12 and being connected at alternating ends, the load monitoring apparatus 10 may comprise any number of tubes to increase the effective length of the bar. It should also be noted that for each added tube to have the same characteristic impedance, i.e., cross sectional area, the thickness of each tube decreases as the number of tubes increases. Attaching the load monitoring apparatus 10 to a direct Hopkinson bar loading system (as the transmitted bar) or to the fixed end of a servo-hydraulic load frame, elimination of high frequency ringing with a long time duration can be achieved efficiently in a fairly short bar.

The load monitoring apparatus 10 can provide increased time duration to achieve large strains. The load monitoring apparatus 10 has the advantage over a conventional long bar in that the stress wave, propagating from the specimen 20, can be transferred into first tube 14 and second tube 16. The first tube 14 and second tube 16 are impedance matched to the solid rod 12 to eliminate the reflection due to the added tubes, and the connection joints 18 are preferred to be small and stiff to reduce the joint reflections. The series of tubes are used about the solid rod 12 for increasing the stress wave duration possible in a given bar length, rather than trapping a shorter stress wave inside a detachable tube.

Figure 2:
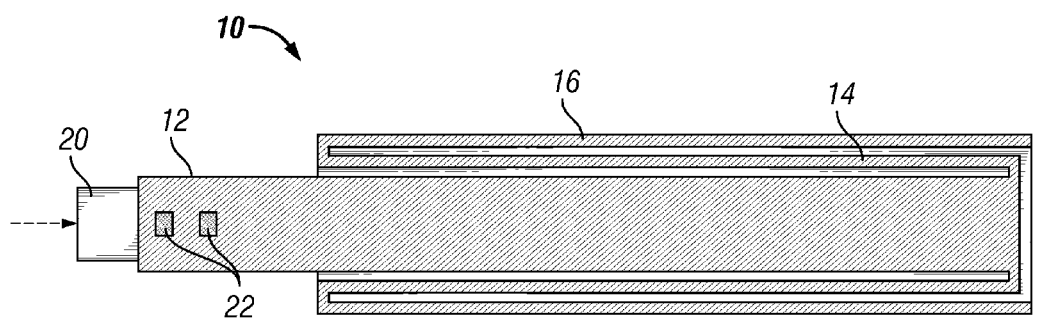
FIG. 2 is a drawing of an example of a cross sectional view of the load monitoring apparatus 10 of FIG. 1 illustrating an impact of a specimen situated at an end of the load monitoring apparatus 10 according to various embodiments of the present disclosure.

Turning now to FIG. 2, shown is a drawing of an example of a cross sectional view of the load monitoring apparatus 10 where a specimen 20 under impact is situated about the proximate end of the solid rod 12 of the load monitoring apparatus 10. The specimen 20 may comprise any type of material suitable for strain-stress testing. The impact on the specimen 20 may be generated by an impacted bar of a conventional Hopkinson bar apparatus and/or any other device suitable for generating an impact on the specimen in use with the load monitoring apparatus 10. During testing, the load monitoring apparatus 10 may comprise one or more sensors 22 that are attached to the solid rod 12 of the load monitoring apparatus 10. The one or more sensors 22 are used to extract the load sampling and reflection monitoring from the load monitoring apparatus 10.

Figure 3:
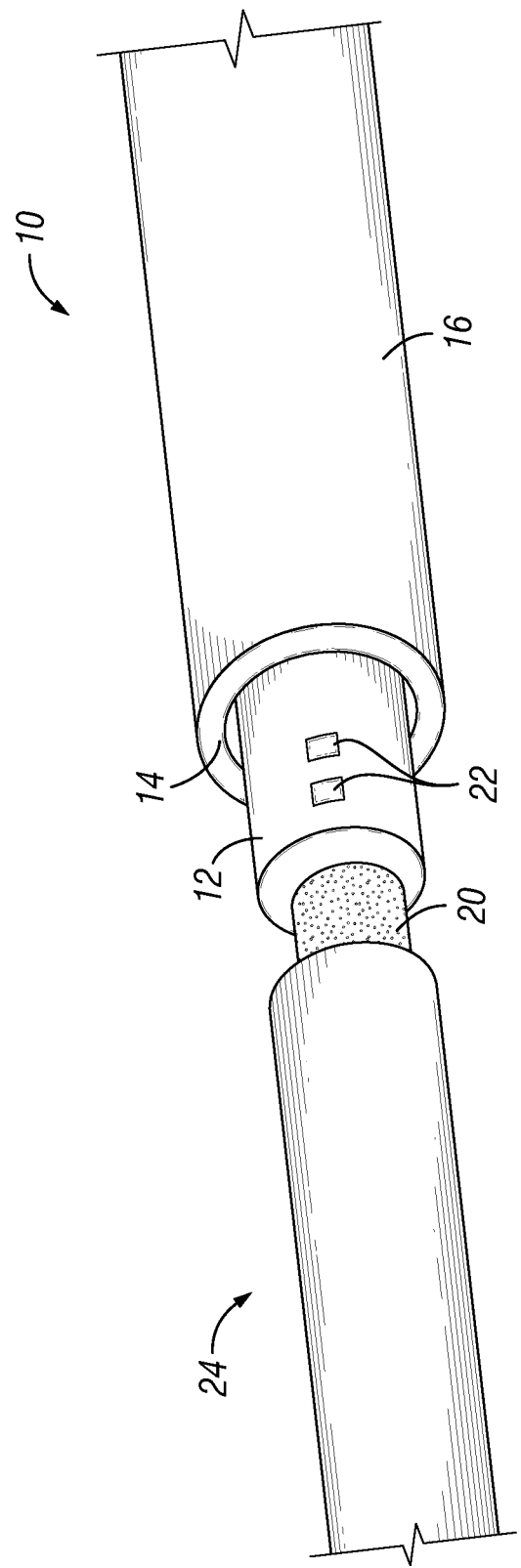
FIG. 3 is a drawing of an example of the load monitoring apparatus 10 of FIG. 1 replacing a conventional transmitted bar in a Hopkinson bar system according to various embodiments of the present disclosure.

Referring next to FIG. 3, shown is a drawing of an example of the load monitoring apparatus 10 in use with an incident member 24 of a Hopkinson bar loading system such that the load monitoring apparatus 10 replaces the conventional transmitted bar. It should be noted that this is just one example of the load monitoring apparatus 10 in use in strain-stress testing. As previously discussed, the load monitoring apparatus 10 may be attached to the fixed end of a servo-hydraulic load frame or any other suitable device that may be used for compression testing and obtaining strain-stress measurements.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A load monitoring apparatus for use in dynamic testing of a material, the load monitoring apparatus comprising:
   a solid rod extending from a proximate end to a distal end;
   a first hollow rod substantially surrounding a portion of the solid rod, the first hollow rod being coupled to the distal end of the solid rod at a first connection point;
   a second hollow rod substantially surrounding the first hollow rod, the second hollow rod being coupled to the first hollow rod at a second connection point, the second connection point being at an opposite end of the first hollow rod from the first connection point;
   and one or more sensors to monitor a load for dynamic testing of the material.

2. The load monitoring apparatus of claim 1, wherein the first connection point and the second connection point each comprise a welded connection.

3. The load monitoring apparatus of claim 1, wherein the first hollow rod and the second hollow rod are impedance matched with the solid rod.

4. The load monitoring apparatus of claim 1, wherein the first hollow rod, the second hollow rod, and the solid rod each have a substantially similar cross sectional area.

5. The load monitoring apparatus of claim 1, wherein the material is situated at the proximate end of the solid rod such that one or more stress-strain mechanical wave signals generated by impact to the material traverses the solid rod, the first hollow rod, and the second hollow rod through the first connection point and the second connection point.

6. The load monitoring apparatus of claim 5, wherein the one or more sensors are attached to the solid rod, the one or more sensors capable of monitoring mechanical load and one or more reflections associated with the one or more stress-strain mechanical wave signals traversing through the load monitoring apparatus.

7. The load monitoring apparatus of claim 1, wherein the solid rod comprises at least one of: steel, steel alloy, aluminum, aluminum alloy, titanium, or titanium alloy.

8. The load monitoring apparatus of claim 1, wherein the first hollow rod and the second hollow rod increase an effective length of the solid rod by a multiple of three.

9. A load monitoring apparatus for testing of a material, the load monitoring apparatus comprising:
   a primary bar;
   a first sensor and a second sensor attached to the primary bar; and
   one or more nested tubes substantially surrounding a portion of the primary bar, the one or more nested tubes being connected in series at alternate ends of the one or more nested tubes;
   wherein the first sensor and the second sensor monitor a load for testing of the material and wherein one or more stress-strain mechanical wave signals are generated by impact to the material.

10. The load monitoring apparatus of claim 9, wherein each of the one or more nested tubes has a substantially similar cross-sectional area as the primary bar.

11. The load monitoring apparatus of claim 9, wherein the primary bar is connected to a first tube of the one or more nested tubes at a distal end of the primary bar.

12. The load monitoring apparatus of claim 9, wherein the one or more nested tubes are connected in series at alternate ends via respective welded connections.

13. The load monitoring apparatus of claim 9, therein the primary bar and the one or more nested tubes are impendence matched.

14. The load monitoring apparatus of claim 9, wherein the first sensor and the second sensor are capable of monitoring one or more mechanical loads associated with the one or more stress-strain mechanical wave signals traversing through the primary bar.

15. The load monitoring apparatus of claim 9, wherein an increase in a quantity of the one or more nested tubes increases an, effective length of the primary bar.

16. The load monitoring apparatus of claim 9, wherein the primary bar is a solid bar comprising at least one of: steel, steel alloy, aluminum, aluminum alloy, titanium, or titanium alloy.

17. The load monitoring apparatus of claim 9, wherein the one or more nested tubes are concentric with the primary bar.

18. A load monitoring apparatus for use in dynamic testing of a material, the load monitoring apparatus comprising:
- a solid rod;
- a plurality of nested tubes substantially surrounding a portion of the solid rod, the plurality of nested tubes being connected in a series at alternate ends of the plurality of nested tubes, a first nested tube of the plurality of nested tubes being directly disposed around the portion of the solid rod and connected to the solid rod via a connection point at an end of the solid rod;
- and one or more sensors to monitor a load for dynamic testing of the material.

19. The load monitoring apparatus of claim 18, wherein the solid rod and the plurality of nested tubes are impedance matched.

20. The load monitoring apparatus of claim 18, wherein the connection point is a welded connection.

* * * * *